United States Patent [19]

Benjamin et al.

[11] Patent Number: 4,975,584

[45] Date of Patent: Dec. 4, 1990

[54] METHOD AND APPARATUS FOR COLLECTING, PROCESSING AND DISPLAYING ULTRAVIOLET RADIATION DATA

[75] Inventors: Thomas L. Benjamin, Boulder, Colo.; Jean J. Robillard, El Paso, Tex.

[73] Assignee: Mountain Ocean, Ltd., Boulder, Colo.

[21] Appl. No.: 329,961

[22] Filed: Mar. 29, 1989

[51] Int. Cl.$^5$ .................. G01J 5/00; G08B 26/00; G08B 27/00
[52] U.S. Cl. ..................... 250/372; 250/339; 250/340; 250/227.11; 340/600
[58] Field of Search ........... 250/372, 339, 340, 227.11; 340/600

[56] References Cited

U.S. PATENT DOCUMENTS

| | | | |
|---|---|---|---|
| 1,845,835 | 2/1932 | Frankenburger | 250/372 |
| 3,710,115 | 1/1973 | Jubb | 250/372 |
| 3,742,240 | 6/1973 | Jonasson | 250/372 |
| 4,428,050 | 1/1984 | Pellegrino et al. | 250/372 X |
| 4,491,727 | 1/1985 | Applebaum et al. | 250/203 R |
| 4,567,367 | 1/1986 | Brown de Colstoun et al. | 250/340 |
| 4,705,046 | 11/1987 | Robillard | 128/665 |
| 4,775,853 | 10/1988 | Perez Bourruate | 250/339 X |

Primary Examiner—Constantine Hannaher
Assistant Examiner—Jacob M. Eisenberg
Attorney, Agent, or Firm—Gary M. Polumbus

[57] ABSTRACT

A system for public display of ultraviolet radiation levels wherein said radiation is collected and measured by one or several optical collectors or sensor assemblies at remote sensing stations. Optical fibers receive and then convey the radiation of the sun through a filter and onto a photovoltaic sensor, measuring the intensity of the ultraviolet radiation. An electrical signal proportional to the ultraviolet radiation is produced with the signal being amplified and either used directly as analog data or converted to a digital signal for the modulation of a radio transceiver. The signal is transmitted to a transceiver of a central data processing station, where it is processed. The processed signal is retransmitted to a receiver in which the processed signal carrier is demodulated and the signal fed to a display station providing the level of exposure to the public.

2 Claims, 5 Drawing Sheets

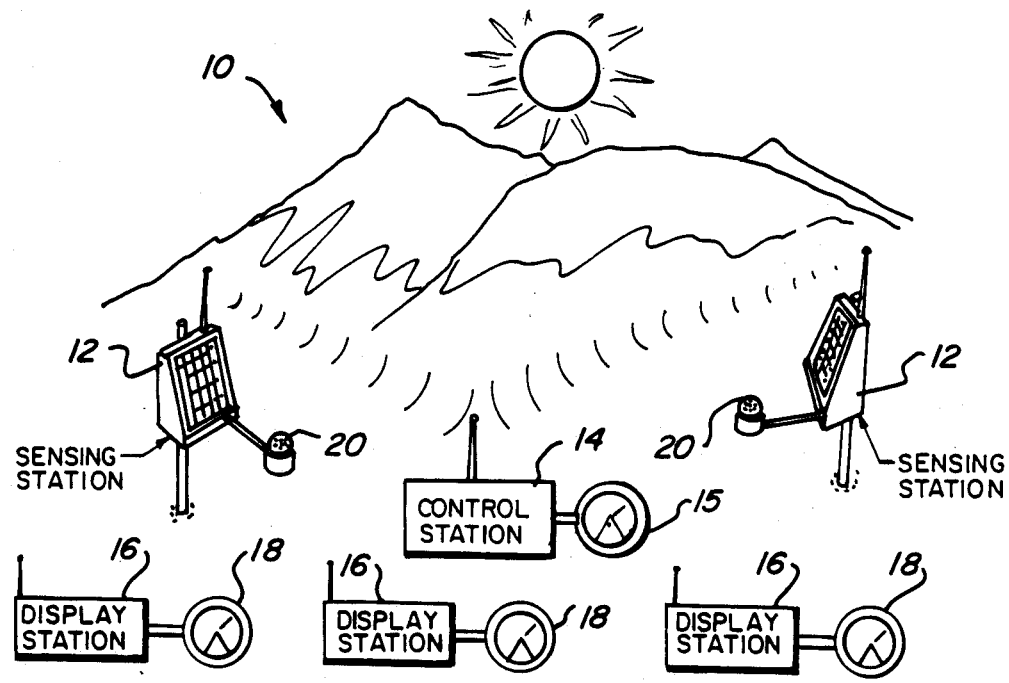
Fig_1
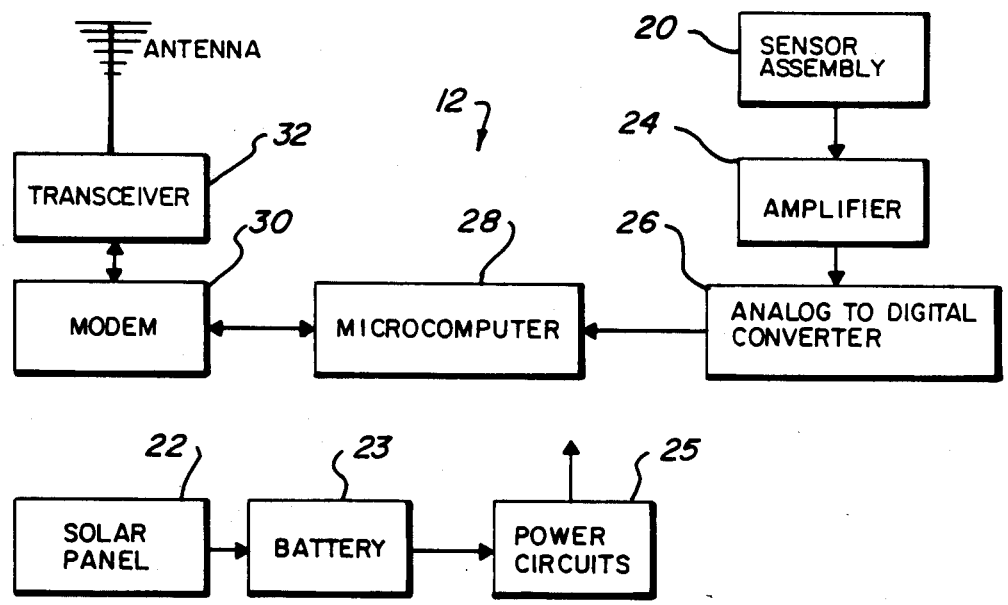
Fig_3

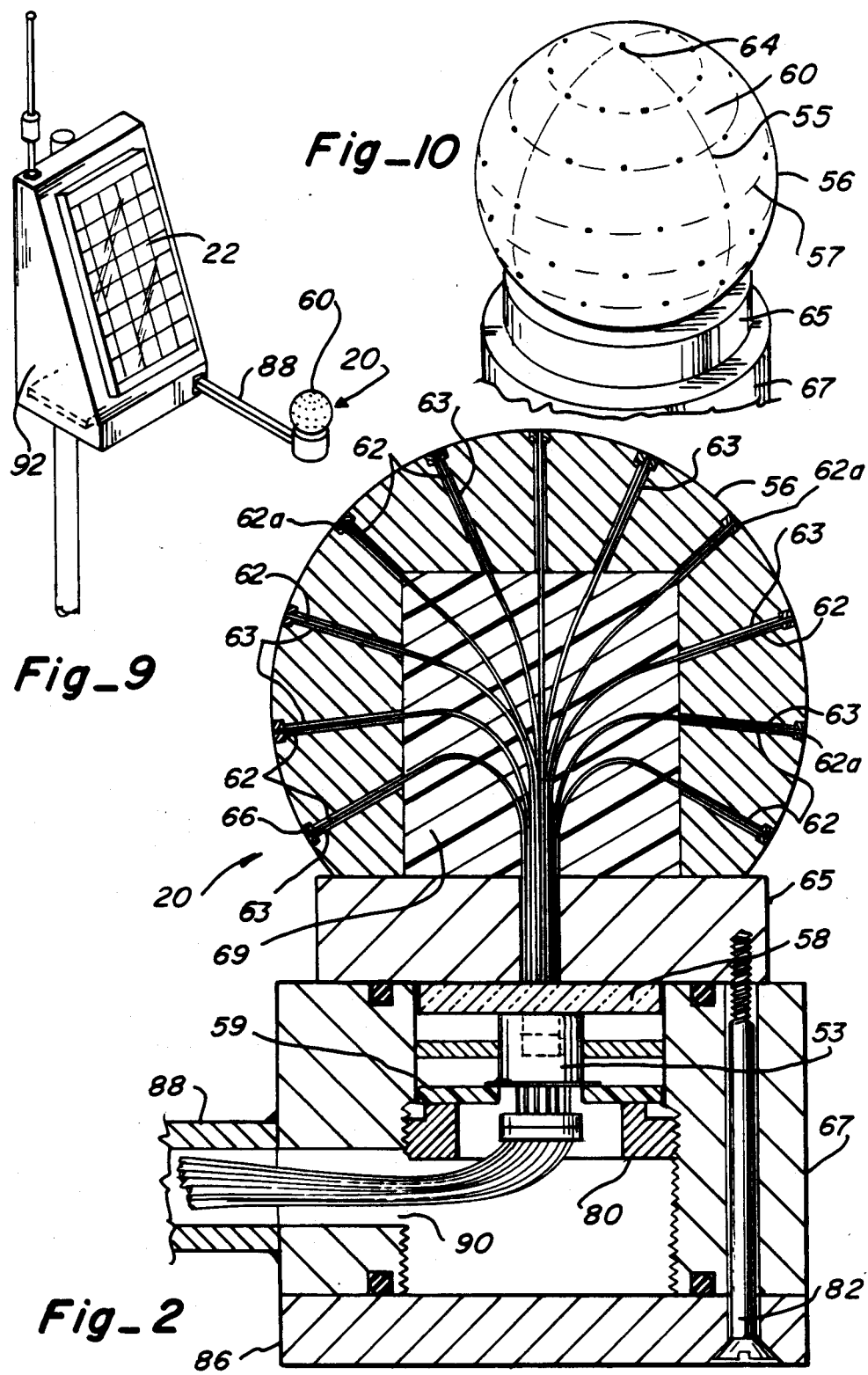

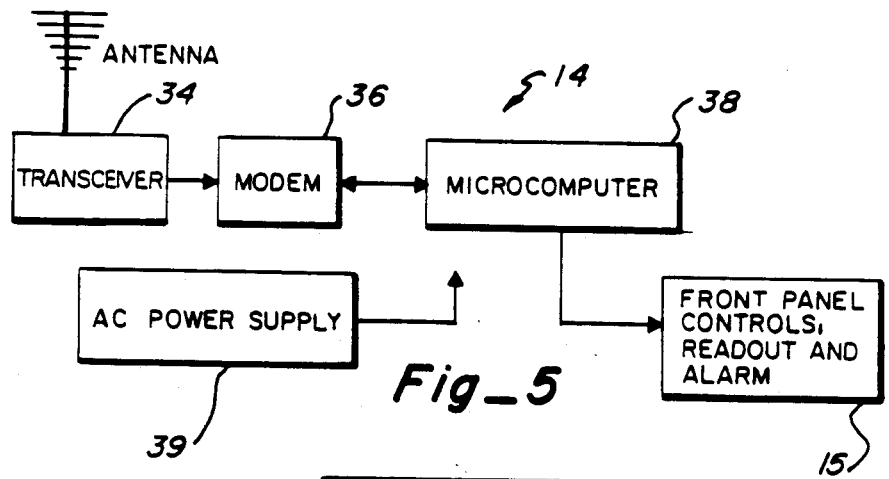
Fig_5
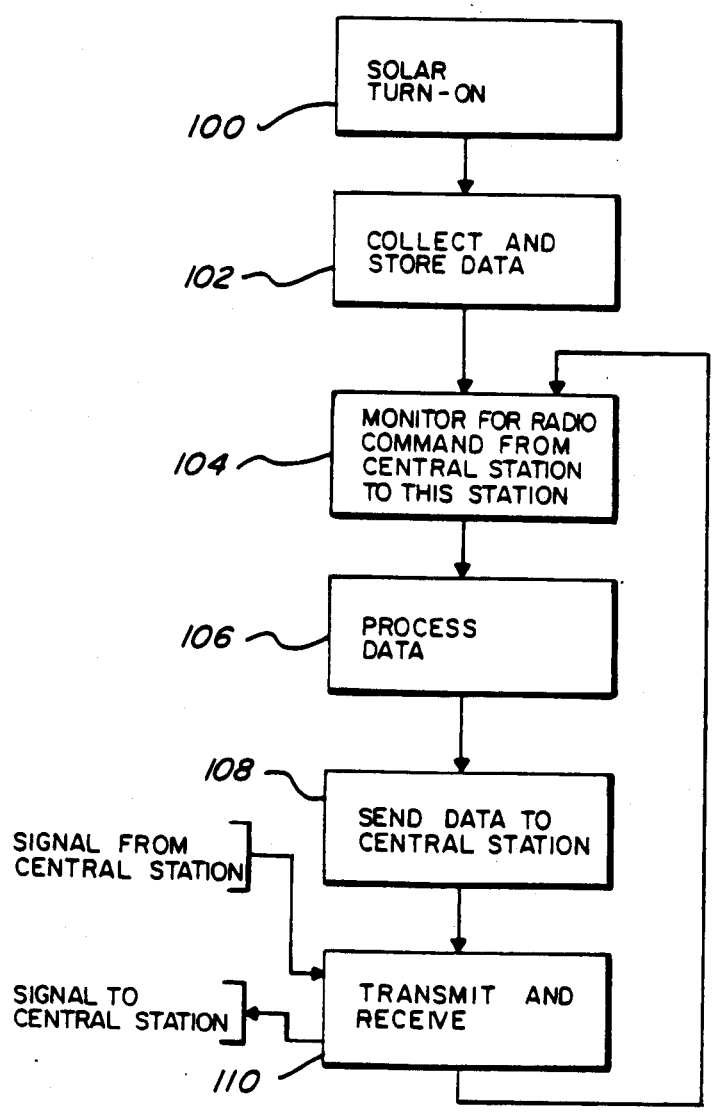
Fig_4

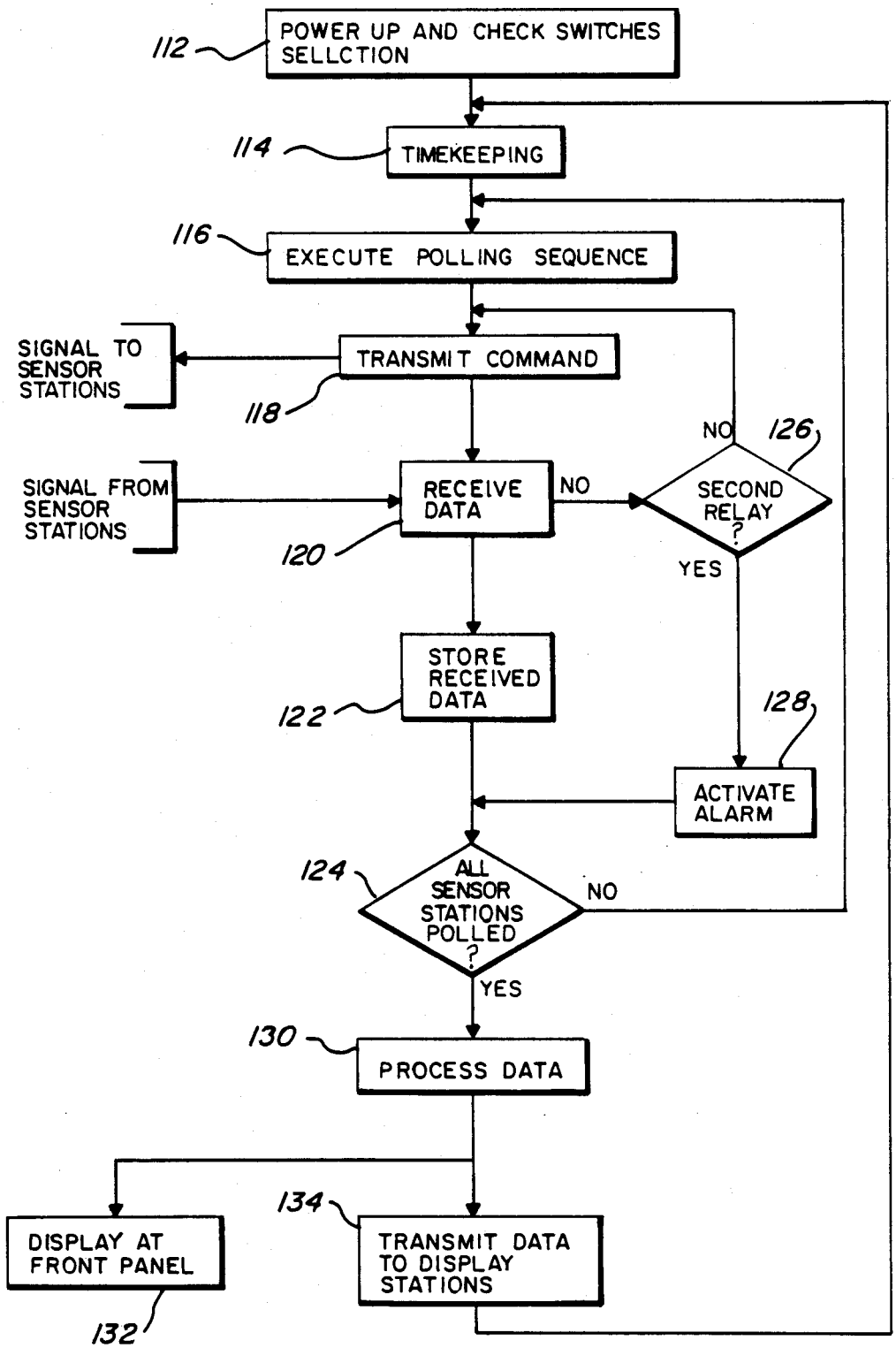
Fig_6

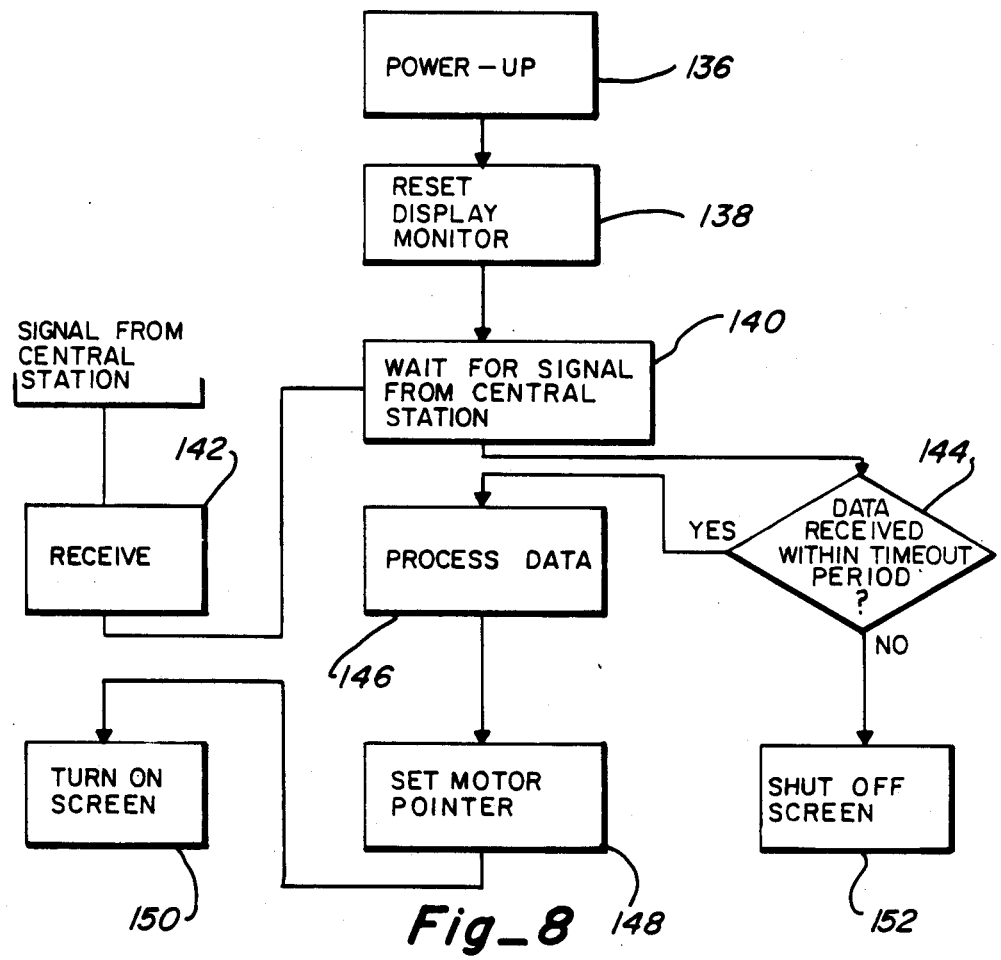
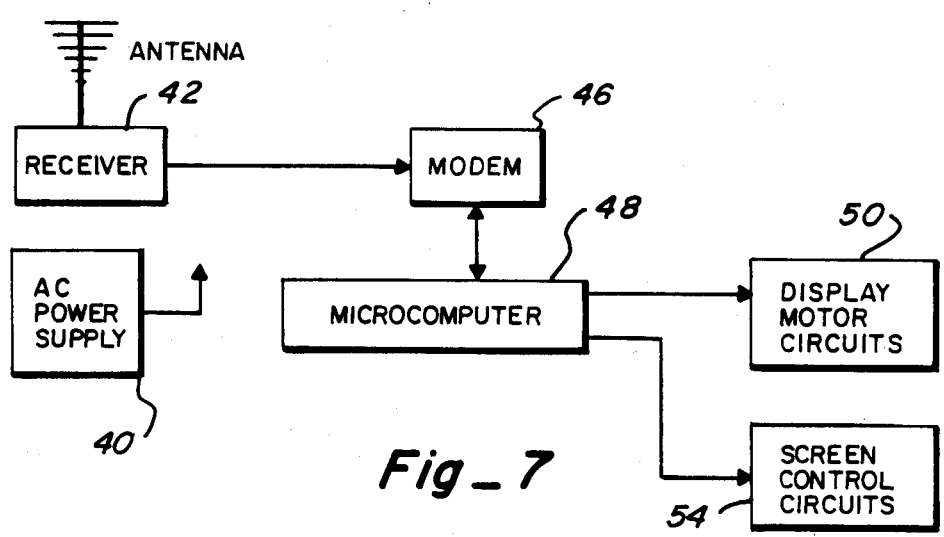

METHOD AND APPARATUS FOR COLLECTING, PROCESSING AND DISPLAYING ULTRAVIOLET RADIATION DATA

BACKGROUND OF THE INVENTION

1. Field of the Invention

The present invention relates generally to the measurement of ultraviolet radiation, such as produced by the sun. More particularly, the present invention relates to collecting, processing and displaying information relating to ultraviolet radiation so that it can be used to warn the public of potential health hazards that may arise from ultraviolet radiation exposure to the sun.

2. Description of the Prior Art

It is desirable to know the relative level of ultraviolet radiation from the sun when engaged in outdoor activities. The damaging effects of exposure to certain ultraviolet wavelengths, in the spectral range of 290 to 320 nanometers, have been recognized for a long time, and a number of methods and devices have been developed to determine a safe exposure. These devices include ultraviolet radiometers, sunburn meters, ultraviolet dosimeters and the like. These devices do not, however, give a wide segment of the public virtually instantaneous warning of the dangers of ultraviolet radiation. No known device displays ultraviolet radiation levels to the public, whether or not those levels are known dangerous wavelengths. Further research may find dangers, or at least the desirability of skin protection, in the broader bandwidth of 290 to 400 nanometers in the ultraviolet range.

Current devices for measurement in the known dangerous range are typically individualized and require elaborate measurement or interpretation, requiring engineering or other technical knowledge to use. In most of the recreational areas where the public is exposed to sunlight, such as ski resorts, beaches or on the deck of a cruise ship, there is little time for objective assessment of the risks of overexposure to ultraviolet radiation. Very often, the danger of sunburn is mistakenly associated with the intensity of the visible light emanating from the sun, and it is well known that the ultraviolet radiation when a sky is covered by haze can be as dangerous as direct sunlight. In addition, the increase in the intensity of ultraviolet rays with altitude does not follow any apparent increase in the visible sunlight. A false impression of safety can be given to the public due to the fact that biological warnings, such as irritation and burning, are often delayed and only occur several hours after exposure.

The dangerous rays, in the spectral range of 290 to 320 nanometers, are transmitted or reflected differently from visible light. The dangerous rays are, therefore, unpredictable, and only devices sensitive to the particular spectral range can provide the necessary information. Examples of such devices include photo detectors sensitive to the particular range of spectrum and which provide a signal proportional to the intensity of the rays received. Devices of this type are described in U.S. Pat. No. 3,710,115, issued to Jubb, and in U.S. Pat. No. 3,742,240, issued to Jonasson. The described devices are provided with integrating circuits to relate the measurement to a maximum dose of exposure. Photochemical detectors showing a gradual color change in a self-integrating device can be calibrated to have optical densities of coloration corresponding to a given dose of radiation Examples of such devices are described by Zweig in British Patent No. 1,507,486; Frankenburger in U.S. Pat. No. 1,845,835; Graham in British Patent No. 1,422,631; Dickinson in British Patent No. 1,573,407; and Robl in German Patent No. 489,671. All of these devices are sensitive to irradiation on the surface of the skin.

Still another photochemical detector provides direct information relative to the reaction of the skin to ultraviolet radiation by measuring the radiation reflected by the skin, as described by J. Robillard in U.S. Pat. No. 4,705,046.

Photo detectors sensitive to the spectral range of 290 to 320 nanometers, described above, measure watts per square centimeter or per square inch and are mostly directed to scientific or atmospheric data collection. Photochemical devices, also as previously described, provide an evaluation only of the dose of the radiation. Such photochemical devices require visual comparison of color densities and, as a result, at least a minimum of attention to the ongoing process. This is a drawback rendering such photochemical devices unsatisfactory for use by the general public. Consequently, there is a need for a quick warning system informing the public of the intensity of ultraviolet radiation and its evolution over a fixed short time period.

SUMMARY OF THE INVENTION

It is, therefore, a principal object of the present invention to provide a system for communicating to the public the relative level of ultraviolet radiation in an accurate and easily understood manner.

It is a related object of the invention to provide a system for displaying ultraviolet radiation level information by determining and measuring levels of ultraviolet radiation at selected sites.

It is another related object of the invention to provide a system for communicating ultraviolet radiation levels wherein ultraviolet data measured at the selected sites is processed to check for errors.

It is a further related object of the invention to provide a system for communicating ultraviolet radiation levels wherein data is processed by integration circuits capable of integrating the data resulting from measurements of ultraviolet radiation over a period of time dependent upon various factors.

It is still a further object of the invention to provide a system for communicating ultraviolet radiation levels wherein collected data is transmitted from selected sites to a central processing station, and from the central processing station to a public display station.

It is still another related object of the invention to provide a system for communication of ultraviolet radiation levels wherein the display of information resulting from collection of ultraviolet radiation data occurs over a specific time in a manner in which quick viewing and assessment of the information is feasible.

The method of the present invention includes the steps of collecting and measuring ultraviolet radiation in the spectral range between 290 and 400 nanometers at a sensor station or collector unit. Measured ultraviolet radiation data, as represented by an electrical signal, is transmitted to a central station where it is processed and integrated over a preselected period of time. From the central station, the resultant signal is transmitted to a display station visible to the public.

Apparatus for performing the method of the invention includes at least one optical ultraviolet sensor associated with at least one sensing station for collecting ultraviolet radiation data in the ultraviolet range. The radiation is focused by a collecting lens or dome by equally spaced optical fibers perpendicularly intersecting a surface of the dome. The fibers are adapted to convey the ultraviolet light received at the surface of the dome to the active area of a photovoltaic sensor. A voltage signal proportional to the intensity of the radiation detected is generated and passed through an amplifier. An analog to digital converter converts the voltage signal into a digital signal which a radio transceiver transmits on request to a central station for data processing.

At the data processing central station, the signals received from the sensing stations are processed. A second radio transceiver transmits the resulting processed data from the central station to one or more public display stations, where a large display provides public information on the level of ultraviolet radiation from the remote sensing stations.

An important advantage of the present invention is that it provides simple, readily interpretable, information on the potential overexposure to damaging ultraviolet rays. Radiation sensors are located at one or more selected sites, and the display stations are located to provide maximum visibility to the public for quick assessment of the information.

Other aspects, features and details of the present invention can be more completely understood by reference to the following detailed description of the preferred embodiment, taken in conjunction with the drawings and from the appended claims.

BRIEF DESCRIPTION OF THE DRAWINGS

FIG. 1 is a diagrammatic perspective view of the ultraviolet radiation detection and display system of the present invention.

FIG. 2 is a sectional view of an ultraviolet sensor assembly.

FIG. 3 is a block diagram of the hardware for a remote sensing station.

FIG. 4 is a flow chart of the software associated with a remote sensing station.

FIG. 5 is a block diagram of the hardware for the central data processing station.

FIG. 6 is a flow chart of the software associated with the central data processing station FIG. 7 is a block diagram of the hardware for a public display station.

FIG. 8 is a flow chart of the software associated with a public display station.

FIG. 9 is a perspective view of a remote sensing station.

FIG. 10 is a fragmentary perspective view of a sensor assembly.

DESCRIPTION OF THE PREFERRED EMBODIMENT

As shown in FIG. 1, a system 10 for collecting, processing and displaying information relating to ultraviolet radiation levels includes a sensing station 12. For purposes of the present disclosure and to obtain a better representation of the various capabilities of the system, two remote sensing stations 12 are disclosed. The ultraviolet radiation data measured at the remote sensing stations 12 is transmitted from the remote sensing stations 12 to a central data processing station 14, where the raw data is received, stored and processed. The control station has a readout 15 where the processed ultraviolet data is displayed in a human readable form.

The processed data is then transmitted from the central station 14 to one or more public display stations 16. The processed data is displayed at stations 16 on meters 18 in a predesigned format easily read by the public. The meters 18 are at various locations, typically a public gateway area, from where the public would disperse or congregate for recreational activities. The meters 18, in the preferred form, would include color coding (not shown), with the colors corresponding to ultraviolet radiation levels. Low ultraviolet radiation levels would possibly correspond to a green area on the meter, medium ultraviolet radiation levels to a yellow area on the meter, and high ultraviolet radiation levels to a red area on the meter 18. The range of ultraviolet radiation level displayed is 290 to 400 nanometers, even though the known damaging range of ultraviolet radiation is 290 to 320 nanometers.

Looking more particularly at a sensing station 12, as shown in FIGS. 1, 2 and 10, an optical collector or ultraviolet sensor assembly 20 is shown as forming a part of the sensing station 12. The sensor assembly 20 collects ultraviolet radiation, focuses the radiation and generates an analog voltage signal proportional to the level of the ultraviolet radiation. With reference to FIG. 3, wherein the hardware for the sensing station is shown in block diagram form, the output voltage analog signal indicative of the intensity of ultraviolet radiation is fed from the sensor assembly 20 to an amplifier 24 of the sensing station 12. The analog signal is then passed through an analog to digital converter 26, a first microcomputer 28, a modem 30, and, finally, to a first radio transceiver 32.

A solar panel 22, shown physically in FIG. 9 and in block form in FIG. 3, generates electrical power so long as the sun is above the horizon, even during overcast conditions. As soon as enough solar radiation is detected as being available, through a conventional power sensing circuit 25, the sensing station 12 is activated. The power circuits 25 also utilize any excess electrical power generated by the solar panel 22 to charge batteries 23.

The functionality achieved by the microcomputer 28 at each solar station 12 is illustrated by the flow chart shown in FIG. 4. Electrical power for operating the microcomputer 28 is obtained from the solar panel 22, and upon receipt of sufficient power, the microcomputer turns on 100. Immediately, the microcomputer commences collecting and storing data 102 by periodically reading the value supplied by the analog to digital converter 26 (FIG. 3) and storing that value in its memory. The periodicity at which the microcomputer 28 reads and obtains new values can be established by software or hardware control associated with the computer 28. Preferably, the computer is programmed to obtain a new value of ultraviolet (UV) radiation approximately once every minute. The software of the microcomputer further associates the values obtained at these intervals with memory locations for other data indicative of the time when those values were collected.

While in the process of collecting and storing the data 102, the microcomputer 28 also is in a loop monitoring for radio command signals from the central station 14 addressed to this particular display station 104. Upon receipt of a command from the central station, this particular station processes the data 106 which it has previously collected and stored 102. Although a number of data processing 106 functions may be programed into the microcomputer 28, the presently preferred embodiment provides two selective options, selected by switches set in the microcomputer. One option is to send 108 the data which has been previously collected and stored 102. The other option is for the microcomputer to calculate an average of the values collected and stored 102 over a predetermined time period which is established by information contained within the command signal sent by the central station. After processing 106, the data is sent 108 by transmitting it 110 to the central station 14. After transmitting the data, the transceiver 32 returns to its normal waiting receive state to be able to receive signals from the central station. All signals received are monitored 104 to determine if they are commands from the central station to this sensing station, and if so, the process 106, 108, 110 is again repeated in accordance with the information contained in the command signal sent from the central station.

As can be seen, therefore, the sensing station is capable of collecting and storing the UV data over predetermined time intervals. The microcomputer 28 of each sensing station then processes the data to either deliver it in raw form or in an averaged form over a time period established by information contained in the command signal sent from the central station. The processed data is then transmitted or sent back to the central station microcomputer where it is thereafter displayed or further processed in accordance with the functionality selected at the central processor. The central station 14, the hardware for which is shown in block diagram form in FIG. 5, includes a second microcomputer 38 interconnected by a modem 36 to a second transceiver 34. The transceiver 34 transmits commands to the sensing station 12, as just discussed, and receives data signals from the sensing station 12. The received signals are processed at the central station 14 and then transmitted by the transceiver 34 to the display station 16.

An A/C power supply 39 supplies power to the central station 14. Outputs of the microcomputer 38 go to a front control panel, which include input switches, the readout 15 and a visual alarm. As will be seen shortly, the readout 15 displays the ultraviolet radiation level in human readable form. Alternatively, the readout 15 gives an error message and a location for the error, indicating that signals are not being received from the sensing station 12. If no signal is received from the sensing station 12, the alarm is illuminated, and the operator told of the need to further investigate the problem.

The operations and functionality of the microcomputer 38 of the central station 14 (FIG. 5) are illustrated in FIG. 6. Upon initially powering the central station 14 on, the microcomputer checks 112 the various switch selections which have previously been set at the front panel 15 (FIG. 5). A time keeping function immediately commences wherein the clock of the microcomputer is utilized as a time base for keeping accurate time during the progress of the day and during particular selected intervals established by the setting of the controls at the front panel. At predetermined intervals established by the switch, the microcomputer commences executing a polling sequence 116 wherein each of the sensing stations will be sent a command which contains information that the sensing stations use in reporting back the UV data, as has been previously described. Commencing the polling sequence involves inserting the necessary information in the command which is transmitted 118 to the sensing stations. After transmitting the command 118, the transceiver of the central station returns to a receive state wherein it is capable of receiving data 120 transmitted from the sensing station. Upon receipt of the data, the received data is stored 122 in memory of the microcomputer of the central station. A determination 124 is thereafter made to determine if all of the sensing stations have been polled. If not, the steps previously described 116, 118, 120, 122 are repeated until all of the sensing stations have been polled.

If the transmission of a command 118 does not result in the reception of a signal 120 from the sensing station within a predetermined time, a retry is executed. The retry consists of again transmitting 118 the command and waiting the predetermined time period to receive the data 120 from the signal from the sensing station. After a second attempt to receive the data from the polled sensing station fails 126, an alarm is activated (128). This alarm appears on the front panel controls of the microcomputer 38 and may be set by switches or software to indicate the failure to receive data from a particular sensing station.

After all of the sensing stations have been polled, and that data which is received from each sensing station has been stored 122, the data may be processed 130. The processing of the data may involve a variety of different functions. For example, in the presently preferred embodiment, the data processed 130 may be that raw data supplied from any one of the sensing stations, or it may be average data supplied by any one of the sensing stations, or the microcomputer of the central station may average the data obtained from one or more of the sensing stations. These options for different data processing 130 functions are, of course, available as software options and are preferably selected by switches or other manual controls at the central station. The processed data 130 is displayed at the front panel 132 of the central station, and is also transmitted 134 to the display stations 16. The data transmitted may be broadcast to all of the display stations, or selected ones of the display stations may be addressed with particular data which they are to display at their locations. The information contained in the transmitted signals identifies and addresses the particular ones or all of the sensing stations.

From the foregoing description, it is apparent that the microcomputer 38 of the central station is capable of polling each of the sensing stations to obtain the data, processing the data in one of a selected variety of manners, and obtaining processed data which is displayed at its front panel and transmitting the data to a display station at a remote location. The data from all of the sensing stations is thus collected or alarm conditions indicating the unavailability of received data from identified sensing stations is made available at the central station.

At each display station 16, a receiver 42 is interconnected to a third microcomputer 48 through a modem 46, as is best seen in the block diagram of the hardware for a display station in FIG. 7. Power is supplied from an A/C power supply 40. The microcomputer 48 operates display motor circuits 50 and screen control circuits 54. The display motor circuits 50 are known circuits which transform the processed ultraviolet data signal received from the central station 14.

The functionality available from the microcomputer 48 at each display station 16 is illustrated by the flow chart of FIG. 8. Upon being powered on 136, a motor associated with a pointer-like display at each display station is reset 138. A waiting state is entered 140 wherein the microcomputer 48 of each display station is waiting for signals from the central station. When the central station transmits to the display station and the signal is received 142, a determination is made 144 of whether the data from the central station is received within a predetermined time out. If so, the data is processed 146. The data processing involves decoding of the information contained in the signal transmitted from the central station to determine that the signal from the central station is addressed to this particular display station. The value of the UV radiation to be displayed at this display station is also derived from the information contained in the signal broadcast from the central station. After this processing, the signals derived are used to set a motor pointer 148 on the display so that the amount of UV radiation to be displayed at this station can readily be perceived and communicated to members of the public.

A shutter-like screen is preferably included in front of the pointer display. This shutter-like screen is, for example, of the liquid crystal diode (LCD) type with an example of a suitable screen being disclosed in U.S. Pat. No. 4,435,047 owned by Raychem. This controllable screen acts as a shutter for allowing viewing of the pointer motor indicating the amount of UV radiation. The screen is turned on 150 to allow this viewing only when the data has been determined 144 to be received within a certain time out period. If the data is not received within a predetermined time out period, the screen is de-energized or shut off 152 to prevent viewing of the pointer display. Through the use of the controllable screen in this manner, and by determining that the data is received or updated within a predetermined time period 144, the accuracy of the data being displayed is better controlled. For example, if the display information is not updated within the predetermined time period, the screen is shut off and the pointer is made unavailable for viewing. This functionality protects against the inadvertent malfunction of the system leaving the display in a particular condition indicating the amount of UV radiation when the malfunction occurred. Since the UV radiation levels may change radically from time to time, the continual updating of the information displayed at the display station assures its accuracy and that previous information will only be displayed for a predetermined time period. The time period during which it is determined 144 that updates have been received can be established by selection through either hardware or software at each display station.

As shown in FIGS. 2, 9 and 10, the ultraviolet sensor assembly 20 includes a collecting lens or optical dome 56, a filter 58, a photovoltaic sensor 53 which is mounted to a PC board 59. Ultraviolet radiation emitted from the sun directly, through cloud formations, or reflected from surfaces in the vicinity are focused on the optical dome 56, which may be made of an opaque plastic such as Delrin, a trademark of DuPont. A surface 60 of the optical dome 56 is intersected perpendicularly by optical fibers 62 fitting into passageways 63 formed through the dome 56. The optical fibers 62 are bonded at 62a or otherwise connected to the surface 60. The dome 56 is bored out to allow for forming the passageways 63 by drilling or other known means. Once the fibers 62 are in place in the passageways 63 and connected at the surface 60 of the dome 56, the bore is filled to receive an insert 69.

The optical fibers 62 connect to the surface 60 of the optical dome 56 at the intersection between fourteen lines of longitude 55 (only a few being illustrated), equally spaced 24° apart, and five lines of latitude 57, also equally spaced 24° apart. (FIG. 10). The lines of latitude 57 define a 120° arc from an apex 64 of the dome 56. The optical fibers 62 are bundled along a central axis of the dome 56 and terminate adjacent the filter 58, for optical communication with the photovoltaic sensor 53.

A platform 65 supports the dome 56 above a base 67. The base 67 carries the photovoltaic sensor 53 and the PC board 59 for holding the sensor 53. A compression ring 80 threadably fits into the base 67 and holds the PC board 59, the sensor 53, and the filter 58 against the platform 65. Opposing bolts 82 (only one being seen) pass through the base 67 and connect the base 67 and a bottom cap 86 to the platform 65 in a sealed relationship via the use of o-rings. A hollow arm 88 integrally connects the base 67 to a sensing station enclosure 92. (FIG. 9). A hollow passageway 90 along the arm 88 and into the sensor 20 allows for passage of wiring from the sensor 20 to the enclosure 92 as seen in FIG. 9.

Although the present invention has been described with a certain degree of particularity, it is understood that the present disclosure has been made by way of example, and changes in detail or structure may be made without departing from the spirit of the invention, as defined in the appended claims.

We claim:

1. An ultraviolet radiation detection and display system, comprising in combination:
   at least one sensing station located at a selected site having ultraviolet radiation sensing means for collecting ultraviolet radiation and producing information in the form of an analog signal proportional to the level of ultraviolet radiation, first microcomputer means for storing said analog signal and having the capability of averaging radiation levels collected over a period of time and for converting said signal to a digital signal, and first transceiver means for transmitting said digital signal and for receiving transmitted input signals;
   a central station having second transceiver means for transmitting input signals to the sensing station and receiving said digital signal from said sensing station, second microcomputer means for processing said digital signal received from said sensing station and having the capability of averaging the information carried by said digital signal with information received from multiple sensing stations, and second transceiver means for further transmitting said processed digital signal; and
   a display station having display means for displaying information indicative of the level of ultraviolet radiation sensed at said sensing station, a receiver for receiving said digital signal from said central station, and third microcomputer means for controlling the display means for displaying said information in a predesigned format.

2. The ultraviolet radiation detection and display system of claim 1 wherein said means for sensing ultraviolet radiation includes a spherically-shaped dome, a plurality of optical fibers perpendicular to and connected at the surface of said dome for conveying said ultraviolet radiation to a predetermined location, a filter mounted at said predetermined location, said filter allowing only ultraviolet rays to pass, and means for converting ultraviolet radiation passed through said filter into signals proportional thereto.

* * * * *